US008967738B2

(12) United States Patent
Blase

(10) Patent No.: US 8,967,738 B2
(45) Date of Patent: Mar. 3, 2015

(54) CUSTOMIZABLE EXPANDABLE STORAGE SYSTEMS FOR THE HOME

(76) Inventor: Gaynell Blase, Houston, TX (US)

( * ) Notice: Subject to any disclaimer, the term of this patent is extended or adjusted under 35 U.S.C. 154(b) by 8 days.

(21) Appl. No.: 13/982,321

(22) PCT Filed: Feb. 16, 2012

(86) PCT No.: PCT/US2012/025359
§ 371 (c)(1),
(2), (4) Date: Jul. 29, 2013

(87) PCT Pub. No.: WO2012/112739
PCT Pub. Date: Aug. 23, 2012

(65) Prior Publication Data
US 2014/0021200 A1    Jan. 23, 2014

Related U.S. Application Data

(60) Provisional application No. 61/443,476, filed on Feb. 16, 2011.

(51) Int. Cl.
| F16B 12/00 | (2006.01) |
| B65D 21/02 | (2006.01) |
| A47B 47/04 | (2006.01) |
| A47F 7/00 | (2006.01) |
| A47F 7/02 | (2006.01) |

(52) U.S. Cl.
CPC ............ B65D 21/0204 (2013.01); A47B 47/04 (2013.01); A47F 7/00 (2013.01); A47F 7/02 (2013.01); B65D 21/0212 (2013.01); A47B 2230/0077 (2013.01)
USPC .............................. 312/111; 211/95; 211/144

(58) Field of Classification Search
CPC .. B65D 25/06; B65D 25/083; B65D 11/1873; B65D 21/0204; B65D 21/0212; A47B 57/00; A47B 47/00; A47B 45/00; A47B 2220/0072; A47B 2230/00; A47B 2230/0074; A47B 2230/007; A47B 2230/0081; A47B 2230/0092; A47B 2230/0096; A47B 2230/07; A47B 96/16; F16B 12/00; F16B 12/10; F16B 12/12
USPC .............. 312/321.5, 107, 108, 109, 111, 245, 312/248, 198, 202, 205, 257.1, 263; 220/4.31, 4.28, 682, 677, 23.4, 23.2; 206/504; 211/50, 53, 58, 78, 144, 186, 211/95; 403/403
See application file for complete search history.

(56) References Cited

U.S. PATENT DOCUMENTS

| 986,395 | A | * | 3/1911 | King | 47/33 |
| 1,468,786 | A | * | 9/1923 | Knechtel | 403/381 |
| 1,833,081 | A | * | 11/1931 | Kilmer | 217/36 |
| 2,011,962 | A | * | 8/1935 | Wheatley | 217/8 |

(Continued)

Primary Examiner — Janet M Wilkens
(74) Attorney, Agent, or Firm — Fox Rothschild LLP; Richard C. Woodbridge

(57) ABSTRACT

A modular storage system (240, 300) is described. A module (10) includes a back panel (12), a left and a right side panel (14a, 14b), and a top and a bottom panel (16). The side panels (14a, 14b,) have a substantially flat outer side and a ridged inner side comprised of alternating evenly spaced pins (18) and tails (20). Multiple modules (10) are connected to each other through various connector means (35, 37, 40) that slidably insert into the tails (20) of the side panels (14a, 14b). Various storage inserts (201, 209, 212, 219, 230, 252) are slidably insertable into the tails 20 of the side panels (14a, 14b). The configuration of the modules (10) and the inserts (201, 209, 212, 219, 230, 252) are customizable.

9 Claims, 13 Drawing Sheets

(56) References Cited

U.S. PATENT DOCUMENTS

| | | | |
|---|---|---|---|
| 2,112,498 A | | 3/1938 | Lax |
| 2,346,430 A | * | 4/1944 | Hauser .......................... 108/27 |
| 2,589,370 A | * | 3/1952 | Grennan ....................... 312/200 |
| 3,288,301 A | * | 11/1966 | Kent et al. ................. 211/41.17 |
| 3,306,689 A | * | 2/1967 | Isaacson et al. ............. 312/199 |
| 3,822,423 A | * | 7/1974 | Watts .............................. 5/201 |
| 4,334,359 A | * | 6/1982 | Kump ........................... 312/111 |
| 4,461,383 A | | 7/1984 | Groff |
| 4,852,741 A | * | 8/1989 | Van Benschoten ........... 206/558 |
| 5,012,943 A | * | 5/1991 | King ............................. 220/4.32 |
| 5,215,205 A | | 6/1993 | Behlman |
| 5,429,430 A | | 7/1995 | Johnson |
| 5,593,058 A | | 1/1997 | Spencer et al. |
| 5,704,508 A | * | 1/1998 | Keip et al. ................... 220/4.31 |
| 6,959,811 B1 | * | 11/2005 | Hoover .................... 206/315.11 |
| D707,989 S | * | 7/2014 | Bezborodko et al. .......... D6/663 |
| 2003/0234229 A1 | * | 12/2003 | Chow et al. ................ 211/41.12 |
| 2008/0218040 A1 | | 9/2008 | Punzel et al. |
| 2010/0155350 A1 | | 6/2010 | Kaplan |

* cited by examiner

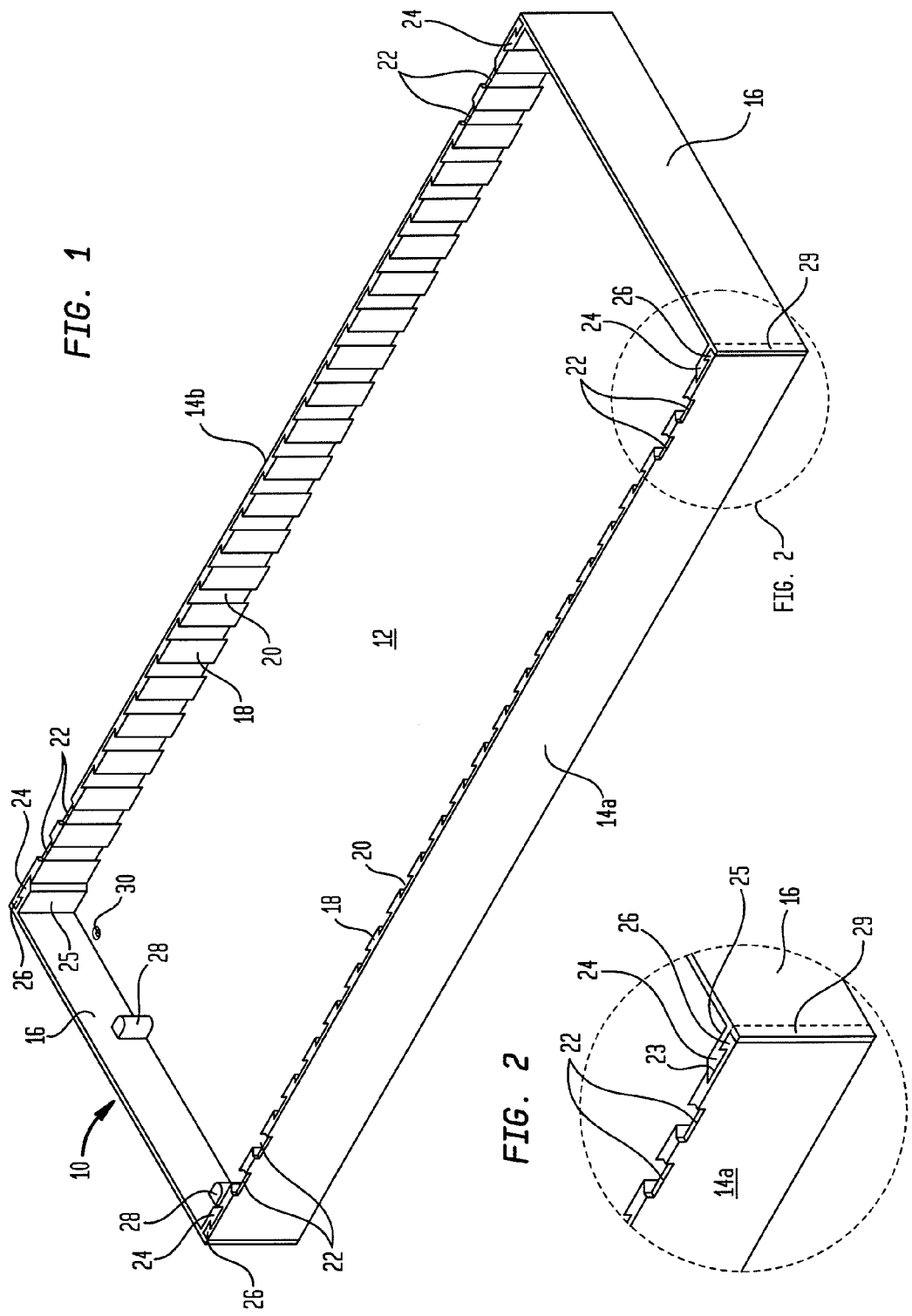

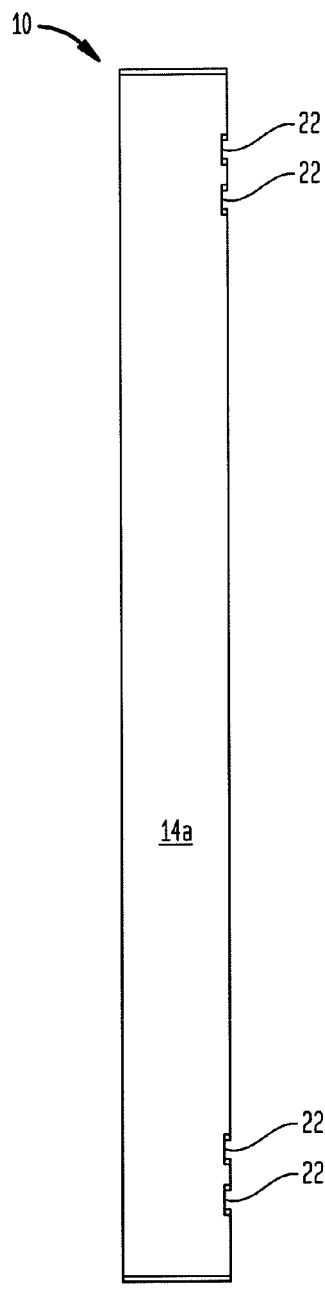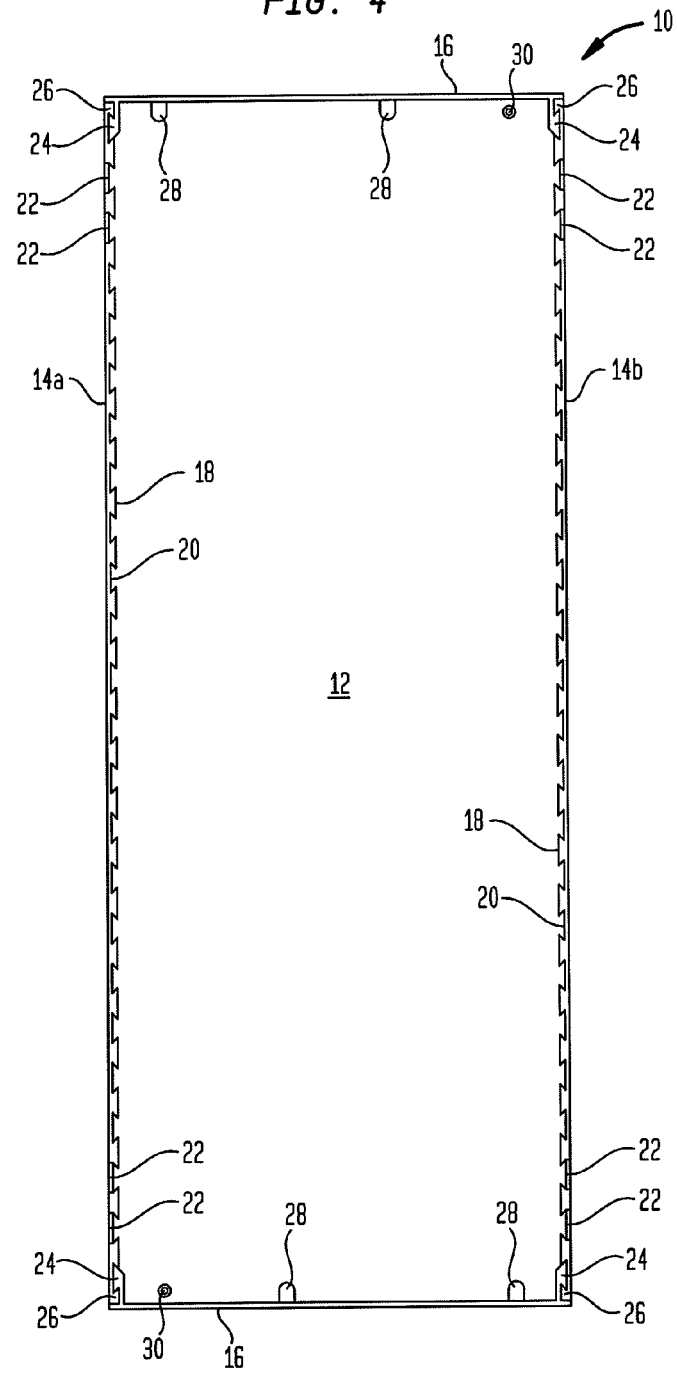

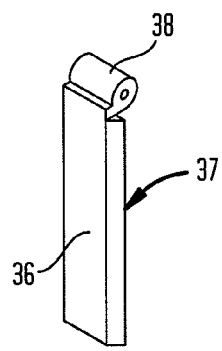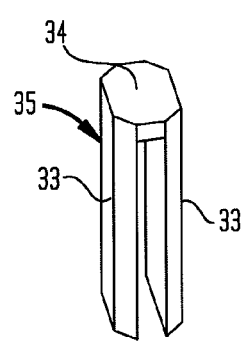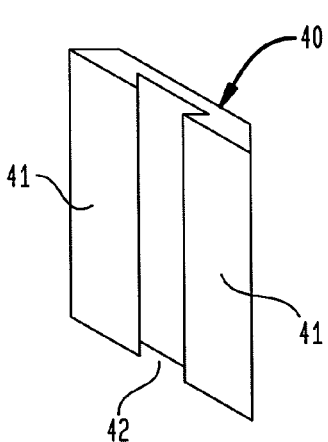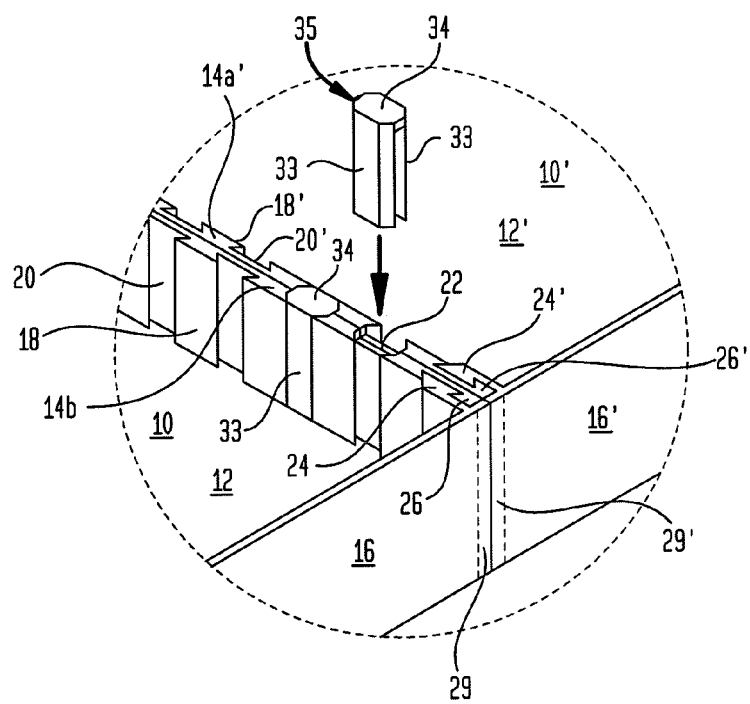

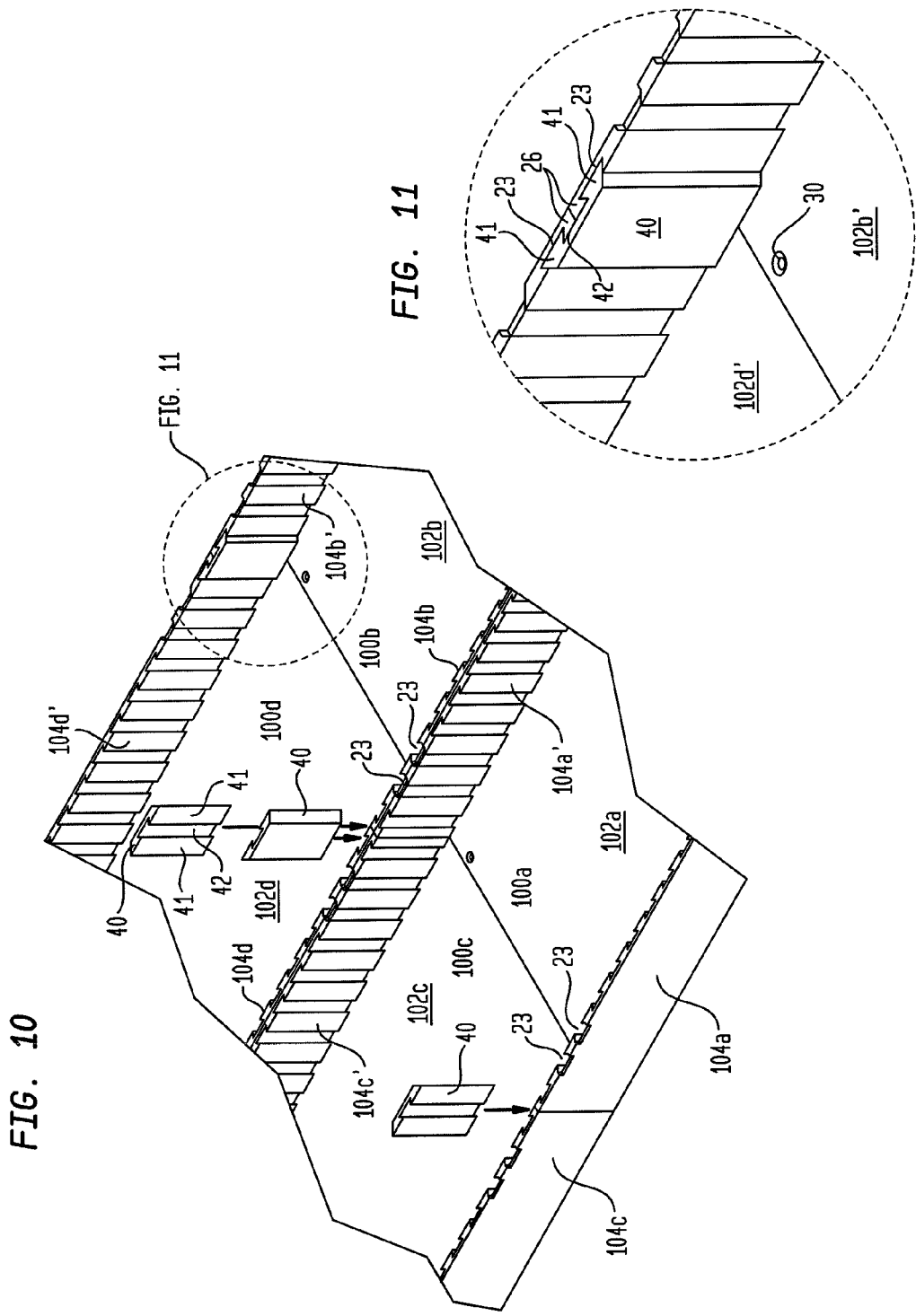

CUSTOMIZABLE EXPANDABLE STORAGE SYSTEMS FOR THE HOME

CROSS-REFERENCE TO RELATED APPLICATIONS

This application is related to and claims priority to PCT Application No. PCT/US2012/025359 filed Feb. 16, 2012, which claims priority to U.S. Provisional Application No. 61/443,476 filed Feb. 16, 2011 entitled "Customizable Expandable Storage Systems for the Home" by Gaynell Blasé, the entire text and substance of which are hereby incorporated in total by reference.

BACKGROUND OF THE INVENTION

1. Statement of the Technical Field

The inventive arrangements relate to modular storage systems, and more particularly, to customizable modular storage assemblies capable of expansion either vertically or horizontally through fixed or pivoted connections and include a variety of inserts.

2. Description of the Related Art

Storage systems adapted to store and display jewelry and other household items are known. However, the current state of the art in storage systems have some significant drawbacks. Most storage cabinets are fixed or limited in the amount of items and types of items that can be stored in the cabinet. The consumer has to work with what is provided for in the cabinet. This can result in unused and wasted space for some types of items or not enough storage space for other types of items. Another problem is once the cabinet is filled, there is no way to add a small amount more of storage space causing the consumer to resort to multiple places for storage of similar items and disorganization. In other cases, the cabinets are of a size that will not fit in the space that is available to the consumer. Still another problem is that most cabinets do not allow the consumer to rearrange and order how items are stored in the cabinets and how many of a certain type of item can be stored.

U.S. Pat. No. 4,978,001 discloses a jewelry closet that includes three portions hinged together in an accordion like fashion. The device can be mounted on a wall. However, the disclosed jewelry closet does not lend itself to a modular construction and does not allow for alternative configurations.

U.S. Patent Application No. 2004/0108796 discloses a modular organizing system having one or more modular storage units for jewelry or personal accessory items. The modular organizing system also includes an interlocking system of mating ribs and depressions for allowing the modular storage units to be stacked and/or aligned horizontally and vertically. The disclosed system, however, exhibits limited customizability and flexibility for storing a wide variety of items.

U.S. Patent Application No. 2010/0224582 discloses a customizable and adjustable shelving assembly with an integral product display, providing an efficient storage system for items of merchandise products. Disadvantageously, the disclosed assembly exhibits a complex construction and is primarily suited for retail product display and not household storage.

U.S. Pat. No. 5,511,873 describes a "Cabinet for the Storage and Display of Jewelry". The cabinet is customizable in that the drawers can be moved up and down to make more or less room for hooks for jewelry and the like. In that sense the drawers and hooks and their location are customizable. However, the disclosed cabinet exhibits only one configuration, and does not allow flexible expansion.

In addition to the references cited above, the following references also appear to be potentially relevant: U.S. Pat. No. 4,413,736; U.S. Pat. No. 4,324,446; U.S. Patent Application No. 2004/0074857; U.S. Pat. No. 4,209,212; U.S. Pat. No. 4,776,650; U.S. Pat. No. 5,087,105; U.S. Pat. No. 5,141,300; U.S. Pat. No. 7,008,029; U.S. Pat. No. 5,758,936; U.S. Pat. No. 6,361,130; U.S. Pat. No. 6,926,136; Japanese Patent Publication No. JP2007006979.

None of the disclosed systems allow for fully customizable sizes and configurations. Therefore, there is a need for a modular storage system that provides flexibility for expansion and full customization of size, depth, and configuration of each module, of the overall system, and of the items to be stored.

SUMMARY OF THE INVENTION

A modular storage assembly is described. The modular storage assembly includes a module that includes a rectangular, substantially flat back panel and a left and a right side panel. The left and right side panels are perpendicularly attached to opposite sides of said rectangular back panel. The left and right side panels have a substantially flat outer side and a ridged inner side comprised of alternating evenly spaced pins and tails.

The modular storage assembly further includes a top and a bottom panel perpendicularly attached to opposite sides of the rectangular back panel and perpendicular to the left and right side panels. The top and bottom panels having a substantially flat outer side and include an extending member at each end that is slidably and/or removably insertable into a first tail from each end of the right and left side panels forming a dovetail joint, wherein the end pin on each side panel forms a flush corner with said top or said bottom panel. The module forms a rectangular open box when fully assembled. Multiple modules may be connected to each other by various connection means to allow customizability and expandability.

The modular storage system is customizable by the consumer in a configuration that best fits consumer's needs and can expand as needs grow utilizing space in a very efficient manner. Modules can vary in size and depth and can attach to each other top to bottom, side to side, back to back and can hinge together. Modules can connect together top to bottom by removing the top and corresponding bottom panels and attaching dual pin vertical connectors. Modules can connect side to side by attaching U-connectors. Modules can hinge together by attaching hinge connectors creating a variety of combinations of single or multiple opening doors. Modules can connect back to back with screws. Modules can hang over a door by attaching over the door hooks or attach to a wall or door with screws. Modules can stand free on the floor.

Inserts such as trays and shelves connect into the cabinets by sliding into the tails of the modules. A variety of inserts are accommodated.

BRIEF DESCRIPTION OF THE DRAWINGS

Embodiments will be described with reference to the following drawing figures, in which like numerals represent like items throughout the figures, and in which:

FIG. 1 is a diagram of a module.
FIG. 2 is a detail diagram of a corner of a module.
FIG. 3 is a side view of a module.
FIG. 4 is a front view of a module.
FIG. 5 is a diagram of a hinge connector.

FIG. 6 is a diagram of a U-connector.

FIG. 7 is diagram of a dual pin vertical connector.

FIG. 8 is a detail diagram of two modules connected with a U-connector.

FIG. 10 is a diagram of two modules connected using a dual pin vertical connector.

FIG. 11 is a detail diagram of two side panels connected using a dual pin vertical connector.

DETAILED DESCRIPTION

Figure 9:
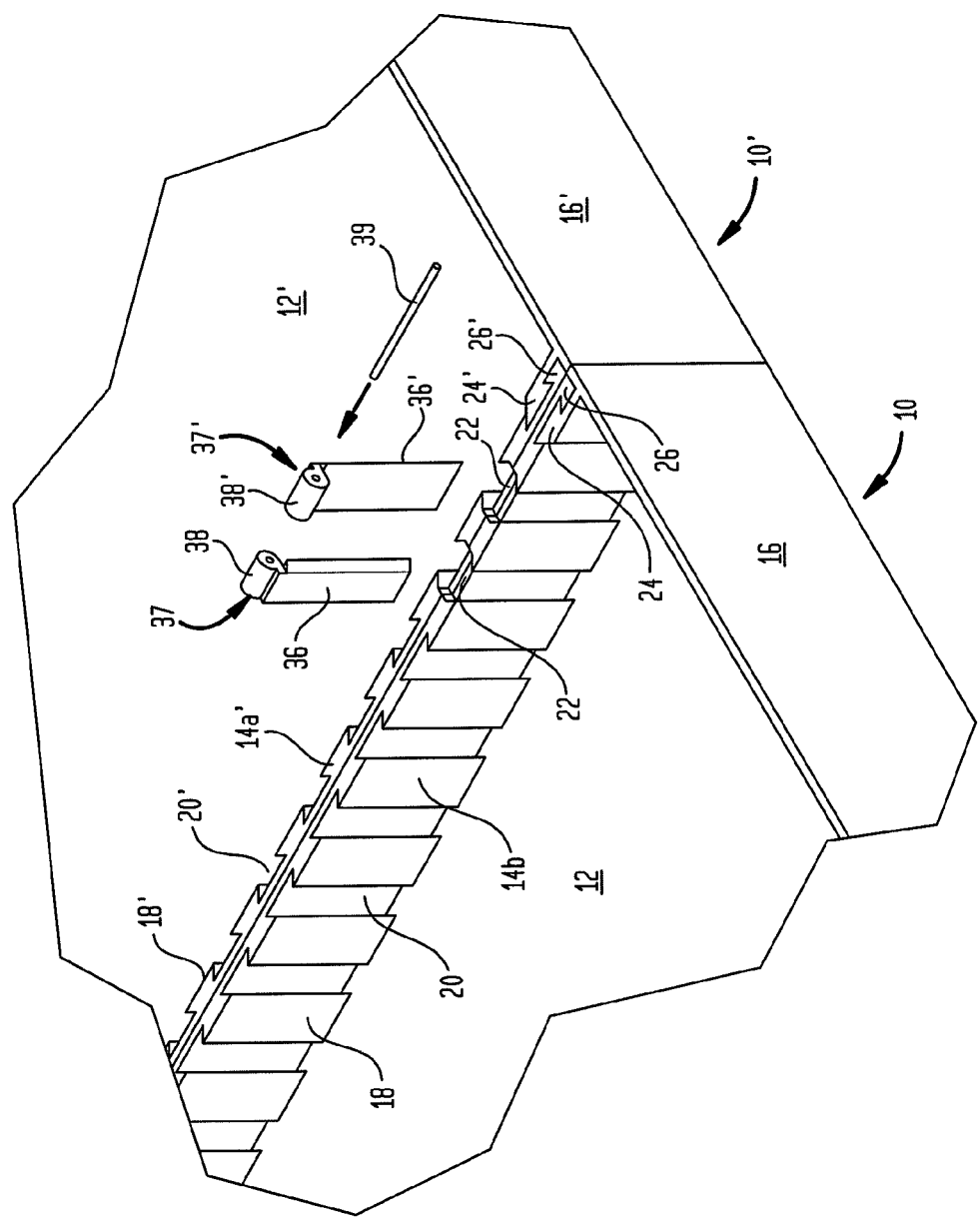
FIG. 9 is a detail diagram of two modules connected with a hinge connector.

The invention is described with reference to the accompanying figures. The figures are not drawn to scale and they are provided merely to illustrate the instant invention. Several aspects of the invention are described below with reference to example applications for illustration. It should be understood that numerous specific details, relationships, and methods are set forth to provide a full understanding of the invention. One having ordinary skill in the relevant art, however, will readily recognize that the invention can be practiced without one or more of the specific details or with other methods. In other instances, well-known structures or operations are not shown in detail to avoid obscuring the invention.

It should also be appreciated that the terminology used herein is for the purpose of describing particular embodiments only and is not intended to be limiting of the invention. As used herein, the singular forms "a", "an" and "the" are intended to include the plural forms as well, unless the context clearly indicates otherwise. Furthermore, to the extent that the terms "including", "includes", "having", "has", "with", or variants thereof are used in either the detailed description and/or the claims, such terms are intended to be inclusive in a manner similar to the term "comprising."

Additional definitions are useful in understanding the embodiments of the present invention. A "dovetail joint" is constructed by slidably interlocking "pins" and "tails". "Pin" and "tail" refer to the structures cut into materials that form dovetail joints. "Pin" refers to the trapezoidal cuts that extend out from the material. "Tail" refers to the trapezoidal indentations that a pin slides into the form the dovetail joint.

Further, unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

Referring to FIG. 1, a diagram of an exemplary embodiment of assembled module 10 is shown. In this embodiment, module 10 includes a substantially flat back panel 12, a left side panel 14a, a right side panel 14b, and top and bottom panels 16. Left and right side panels 14a, 14b, include alternating pins 18 and tails 20. As is shown in FIG. 1, the pins and tails alternate throughout the span of left and right side panels 14a, 14b. Further, in the exemplary embodiment illustrated in FIG. 1, at least two notched tails 22 that include notches cut into the outward side of left and right side panels at positions near each end of each panel. In some embodiments, more than four tails are notched. In further embodiments, all tails are notched. Top/bottom panels 16 include an extending member 25 that is comprised of a pin 24. Top/bottom panels 16 also includes at least one blind hole 30 and at least one boss 28. Blind holes on the back panel have the appearance of a solid panel. However they may be punched out with minimal effort if needed for attaching module 10 to a wall, a door hanger, another module 10, and the like. In certain embodiments, one or more blind holes 30 may be aligned with one or more bosses 28.

Module 10 is constructed by joining top and bottom panels 16 to the left and right side panels 14a, 14b as shown in FIG. 2. Referring now to FIG. 2, a magnified view of a corner of module 10 is shown. As shown in FIG. 2, left side panel 14a includes at least two notches 22, and an end tail 23 and an end pin 26. Bottom panel 16 includes an extending member 25 that includes a pin 24. The joint between left side panel 14a and bottom panel 16 is made by sliding the pin 24 of bottom panel 16 into the end tail 23 of left side panel 14a. Further, end pin 26 of left side panel 14a inserts into the tail formed between pin 24 and extending surface 29. This same construction occurs at all four corners of module 10 and connects top/bottom panels 16 to each side of left and right side panels 14a, 14b. FIGS. 3 and 4 illustrate additional views of module 10, from a side view and a front view respectively.

Embodiments may include different configurations of the top/bottom panel 16 without departing from the inventive concepts described herein. For example, one embodiment may include a top/bottom panel 16 that does not include extending surface 29. In this exemplary embodiment, the top/bottom panel 16 fits between side panels 14a, 14b and back panel 12, and can be repositioned within the module to function as a shelf. In another exemplary embodiment, additional extending surfaces (not shown in FIG. 2) may extend perpendicular from top/bottom panel 16 and along back panel 12. In yet another exemplary embodiment, all extending surfaces of top/bottom panel 16 may be perforated and break off from top/bottom panel 16.

Module 10 forms a single modular customizable and expandable unit in a modular storage system. As stated above, module 10 is not illustrated to scale in FIGS. 1-4. One of skill in the art will recognize that the back panel 12, side panels 14a, 14b, and top panels 16 can be of any practical size, length, width, and depth without departing from the scope and spirit of the inventive embodiments. Further, as described below, inserts can be devised to be slidably and/or removably insertable into the tails of side panels 14a, 14b. For example, module 10 can be deep and wide enough to accommodate slidably and/or removably insertable shelving units for shoe storage. Alternatively, the module 10 can be adapted to store any variety of items. Further modules may be connected back to back using blind holes 30 and bosses 28 with any connecting means, such as screws, for example.

Multiple modules 10 can be connected through connector means in vertical and horizontal directions and can be joined together to expand depth-wise. Referring now to FIGS. 5-7, exemplary connector means are shown. FIG. 5 illustrates a hinge connector 37. The hinge connector 37 includes the hinge cylinder 38 and pin 36. The pin 36 is slidably and/or removably insertable into one of notched tails 22. One skilled in the art will recognize that two hinge connectors can be inserted, one into one notched tail 22 in a first module and the other into a notched tail 22 in a second module to form a pivotally hinged connection. The hinge is completed by inserting a rod (not shown in FIG. 5) into the hinge cylinder 38 of both hinge connectors. This connection means is described in further detail below in reference to FIG. 9.

Referring now to FIG. 6, a U-connector 35 is shown. The U-connector 35 includes a connector surface 34 and two connector pins 33. The connector pins 33 are slidably and/or removably insertable into notched tails 22. U-connector connects two modules together horizontally in a fixed manner. This connection means is described in further detail below in reference to FIG. 8.

Referring now to FIG. 7, a dual pin vertical connector 40. The dual pin vertical connector 40 includes two vertical connector pins 41 and a vertical connector tail 42. The vertical connector pins 41 are slidably and/or removably insertable into the end tails of two left side panels or two right side panels. This allows for two modules to be vertically connected. The two end pins of the respective side panels combine to form one pin that is slidably and/or removably insertable into vertical connector tail 42. This connection means is described in further detail below in reference to FIGS. 10 and 11.

Referring now to FIG. 8, a connection of two modules 10, 10' with a U-connector 35 is shown. As described above, each module is comprised of a substantially flat back panels 12, 12', a top/bottom panels 16, 16', a left side panels 14a (not shown), 14a', and right side panel 14b, 14b' (not shown). Right and left side panels 14b, 14a' include pins 18, 18', tails 20, 20', and notched tails 22. The joint between the right and left side panels 14b, 14a' and the top/bottom panels 16, 16' is made in a similar way as described above in reference to FIG. 2.

As shown in FIG. 8, a U-connector 35 is slidably and/or removably inserted into notched tails 22. Connector surface 34 and the surface of pins 33 form a flush surface with the right and left side panels 14b, 14a'. In this way, modules 10, 10' are fixedly connected in a horizontal configuration. Although the above horizontal connection is described in terms of two modules, one of skill in the art will recognize that such a connection can be made with any number of modules arranged in a horizontal configuration. The embodiments of the present invention are not limited in this regard.

Referring now to FIG. 9, a connection of two modules 10, 10' with a hinge connector is shown. Each module is constructed in a manner similar to that described above in reference to FIG. 8. As shown in FIG. 9, the modules 10, 10' are connected with two hinge connectors 37, 37' slidably and/or removably inserted into notched tails 22 of the right side panel 14b of module 10 and the left side panel 14a' of module 10'. A rod 39 is inserted into hinge cylinders 38, 38' to form a complete hinge. The modules are now pivotally connected in a horizontal configuration. This configuration allows the modules to be folded into a closed unit. Further, module 10 and module 10' can be of different sizes. For example, module 10 can be a shallow module and module 10' can be a deep module. In this example, module 10 is configured as a customizable door for module 10'.

Referring now to FIG. 10, a dual pin vertical connector 40 is shown for connecting modules vertically. As described above, the dual pin vertical connector 40 includes two vertical connector pins 41 and a vertical connector tail 42. As shown in FIG. 10, modules 100a and 100c are connected together using vertical connectors 40. Additionally, modules 100b and 100d are connected together using vertical connectors 40. Modules 100a-d include similar components as those of module 10. Each module includes a substantially flat back panel 102a-d and right and left side panels 106a-d, 106a'-d'. For purposes of illustration the top/bottom panels of the module assembly are not shown in FIG. 10. They are described in further detail below in reference to FIGS. 12-14.

As shown in FIG. 10, the dual pin vertical connector 40 is slidably and/or removably insertable into the end tails 23 of left and right side panels 106a-d, 106a'-d'. Referring now to FIG. 11, a detail of one such joint is shown. In FIG. 11, dual pin vertical connector 40 connects side panels 104b' and 104d'. Vertical connector pins 41 are slidably and/or removably insertable into end tails 23 of each side panel 104b', 104d'. The end pins 26 of each side panel form a complete pin that is slidably and/or removably insertable into vertical connector tail 41 of dual pin vertical connector 40.

As can be seen in FIGS. 10 and 11, the dual pin vertical connector 40 allows for expandability of the customizable module 10 vertically and may be combined with the U-connector 35 (as shown in FIG. 8) to add strength and stability to the vertical joints. Although the above vertical connection is described in terms of two modules, one of skill in the art will recognize that such a connection can be made with any number of modules arranged in a vertical configuration. The embodiments of the present invention are not limited in this regard.

Figure 12:
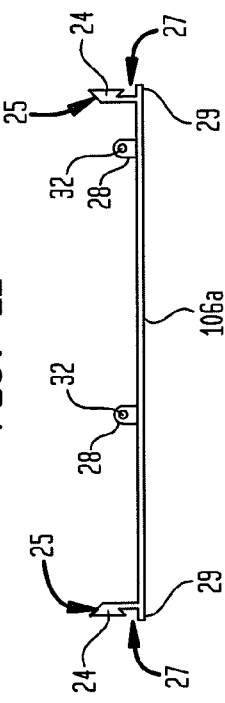
FIG. 12 is a diagram of a single wide top/bottom panel.
Figure 13:
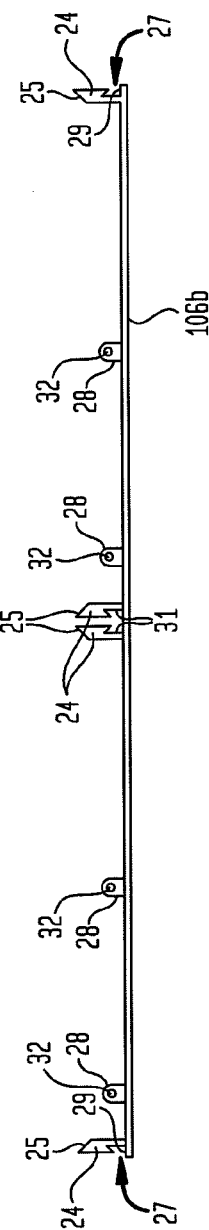
FIG. 13 is a diagram of a double wide top/bottom panel.
Figure 14:
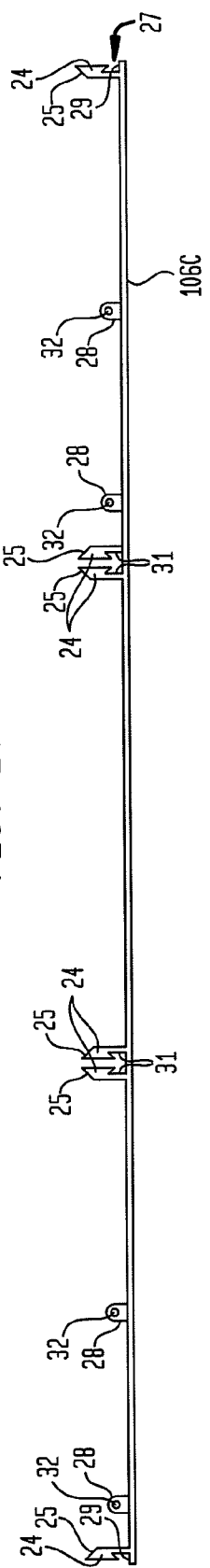
FIG. 14 is a diagram of a triple wide top/bottom panel.

Referring now to FIGS. 12-14, embodiments of the top/bottom panels 106a-c are shown. FIG. 12 shows the single wide top/bottom panel 106a. Top/bottom panel 106a is similar to top/bottom panel 16 of FIG. 1. Top/bottom panel includes two extending members 25, one near each end of top/bottom panel 106a. Each end of top/bottom panel 106a includes an extending surface 29. On each end a top/bottom end tail 27 is formed between the extending surface 29 and the extending member 25. In certain embodiments, extending surface 29 is detachable from single wide top/bottom panel 106a. Further, top/bottom panel 106 includes at least one boss 28 and at least one hole 32 bored in boss 28. The bosses 28 allow for sturdy connections with back panels 12 through any appropriate connection means, such as screws for example. As described above, the bosses 28 align with blind holes 30 on back panels 12. This configuration also allows for connection of door hanging means and/or back to back attachment of modules.

Referring now to FIG. 13, a second embodiment of a top/bottom panel, double wide top/bottom panel 106b. This embodiment includes similar features as single wide top/bottom panel 106a, described above in reference to FIG. 12. However, double wide top/bottom panel 106b further includes two extending members 25 near the mid-point of top/bottom panel 106b and forming inner top/bottom end tails 31. One skilled in the art will note that the end pins 26, 26' as shown in FIG. 8 are slidably and/or removably insertable into inner top/bottom end tails 31 to form a joint between right and left side panels 14b, 14a' as shown in FIG. 8 and double wide top/bottom panel 106b of FIG. 13. As with single wide top/bottom panel 106, extending surface 29 of double wide top/bottom panel 106b may be detachable in some embodiments. As can be seen in FIG. 13, double wide top/bottom panel is able to accommodate two modules arranged horizontally.

Referring now to FIG. 14, another embodiment of a top/bottom panel, triple wide top/bottom panel 106c. This embodiment includes similar features as single wide top/bottom panel 106a of FIG. 12 and double wide top/bottom panel 106b of FIG. 13. However, triple wide top/bottom panel 106c further includes two additional extending members 25 (for a total of four) forming additional inner top/bottom end tails 31. As mentioned above in reference to FIGS. 12 and 13, extending surface 29 of triple wide top/bottom panel 106c may be detachable in certain embodiments. As can be seen from FIG. 13, triple wide top/bottom panel 106c is able to accommodate three modules arranged horizontally.

One of skill in the art will recognize that the above described parts may be arranged in any combination and configuration to provide a flexible, expandable, and customizable storage system. Further, the modules may be affixed to a wall, to a door via a door hanger, or be stand alone.

In addition to customizable expansion and size, embodiments of the inventive storage system include a plurality of slidable inserts that include at least one pin on either side to be slidably and/or removably insertable into tails 20 of module 10. These inserts may be of any size and shape without departing from the scope of the present invention. These inserts can include trays, peg boards, hooks, restraining bars, rods, and/or any other form useful for storing items. Items which may be stored via the inserts include jewelry, hardware, shoes, tools, clothing, ties, fishing equipment (including poles, tackle, etc.), audio/visual media (including compact discs (CDs), digital versatile discs (DVDs), blu-ray discs (BDs), videotapes, etc.), and/or any other household or personal item. The embodiments of the present invention are not limited in this regard.

Figure 15:
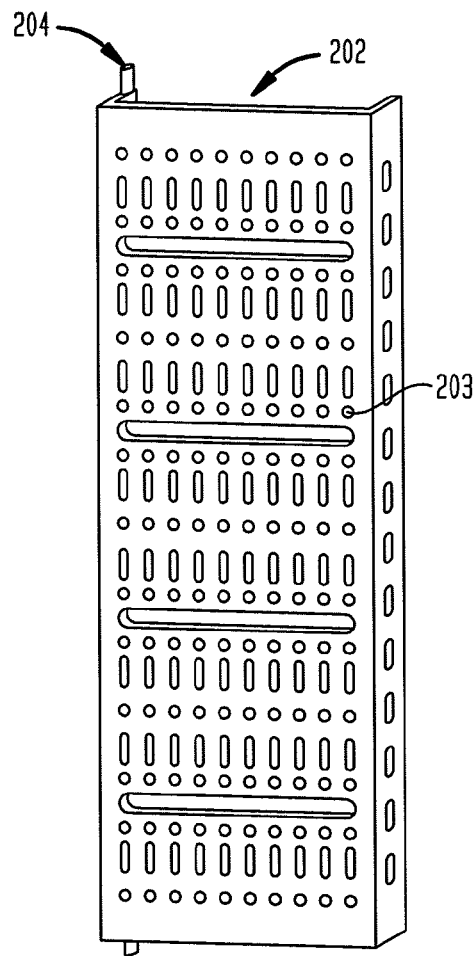
FIG. 15 is a diagram of a vertical flag.
Figure 16:
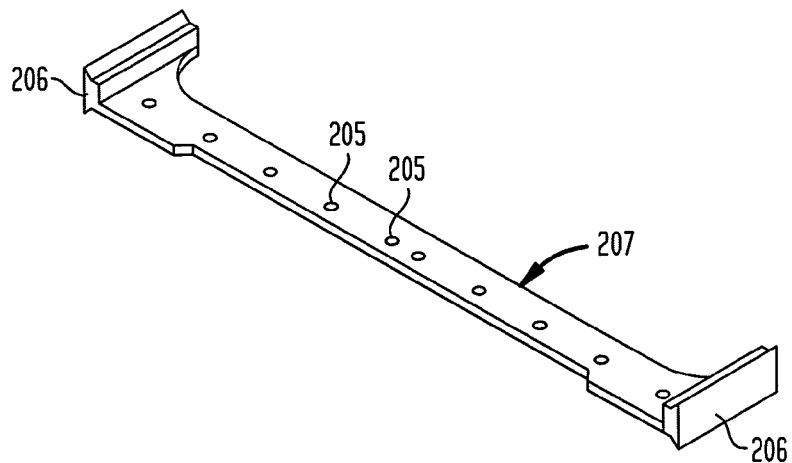
FIG. 16 is a diagram of a flag support bar.
Figure 17:
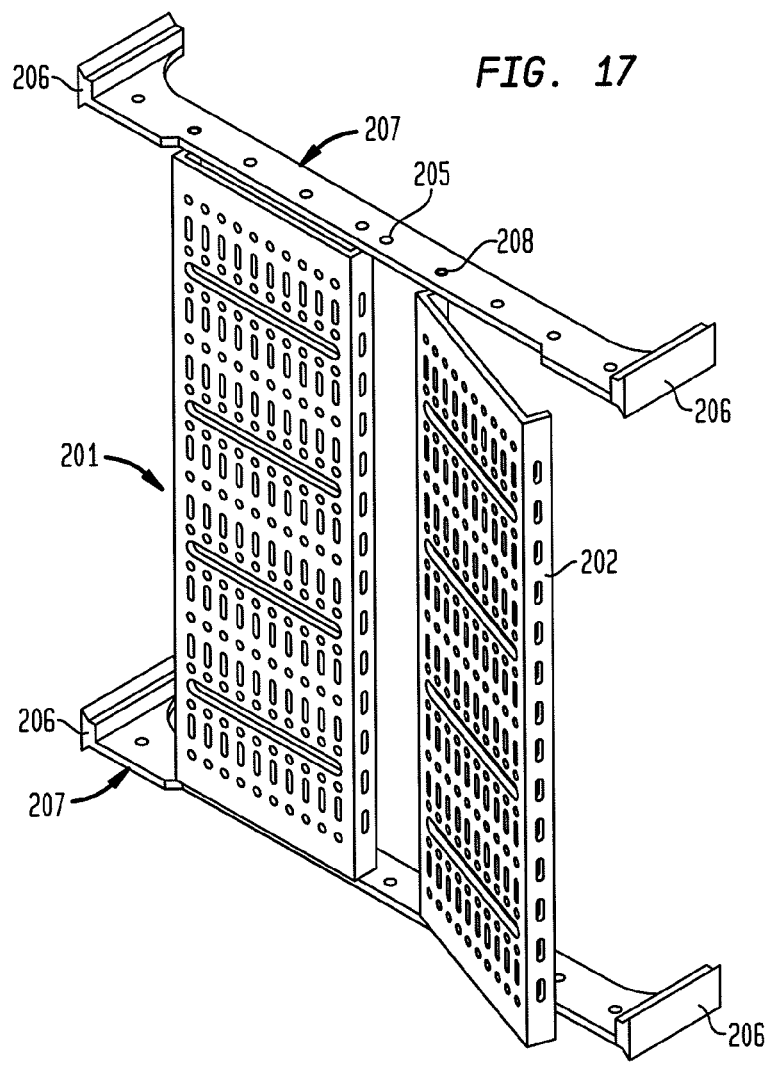
FIG. 17 is a diagram of a flag insert.

Referring to FIGS. 15-20, exemplary embodiments of various slidably and/or removably insertable inserts are provided. Referring to FIG. 17, a flag insert 201 is shown. FIGS. 15 and 16 show the components of flag insert 201. Referring to FIG. 15, a vertical panel or flag 202 is shown. Flag 202 includes a plurality of holes and slots 203 throughout the surface of flag 202 and pegs 204 at the top and bottom of flag 202. Referring FIG. 16, a horizontal member or flag support bar 207 is shown. Flag support bar 207 includes a plurality of holes 205 and flag end pins 206. As shown in FIG. 17, pegs 204 of flag 202 insert into one of the plurality of holes 205 on each of two flag support bars 207 to form the completed flag insert 201. As shown in FIG. 17, peg 204 can be slidably and/or removably inserted into one of holes 205. In an embodiment, peg 204 is round. One of skill in the art will notice that pins 206 on each end of flag support bars 207 are slidably and/or removably insertable into appropriate tails 20 of module 10. Although flag insert 201 is shown with holes and slots 203 that are useful for hanging earrings, the embodiments of the present invention are not limited in this regard. For example, flag 202 may include a plurality of hooks or may be comprised of a peg board.

Figure 18:
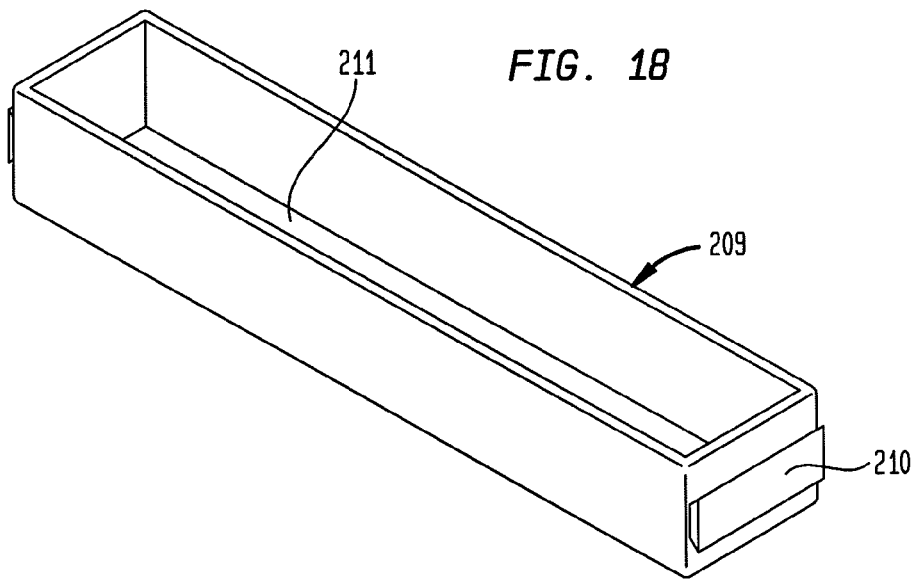
FIG. 18 is a diagram of a tray insert.

Referring to FIG. 18, a tray insert 209 is shown. Tray insert includes a tray cavity 211 and tray end pins 210. Tray end pins 210 are adapted to slidably and/or removably insert into tails 20 of module 10. Tray insert 209 as shown is a rectangular tray. One of skill in the art will recognize that the size and shape of a tray insert is not limited to that illustrated in FIG. 18.

Figure 19A:
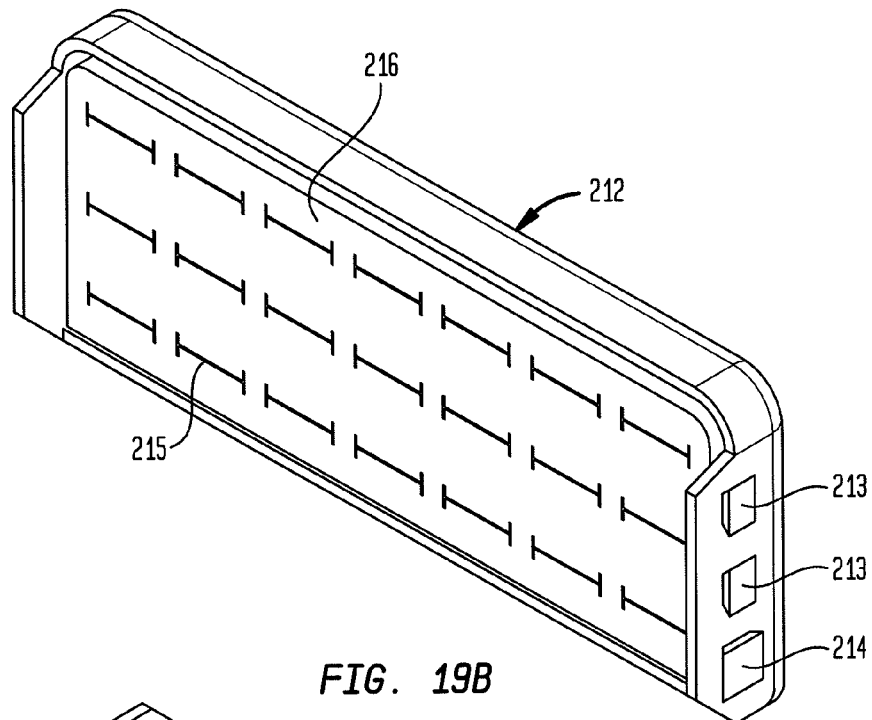
FIG. 19a-b are diagrams of a flat tray insert.
Figure 19B:
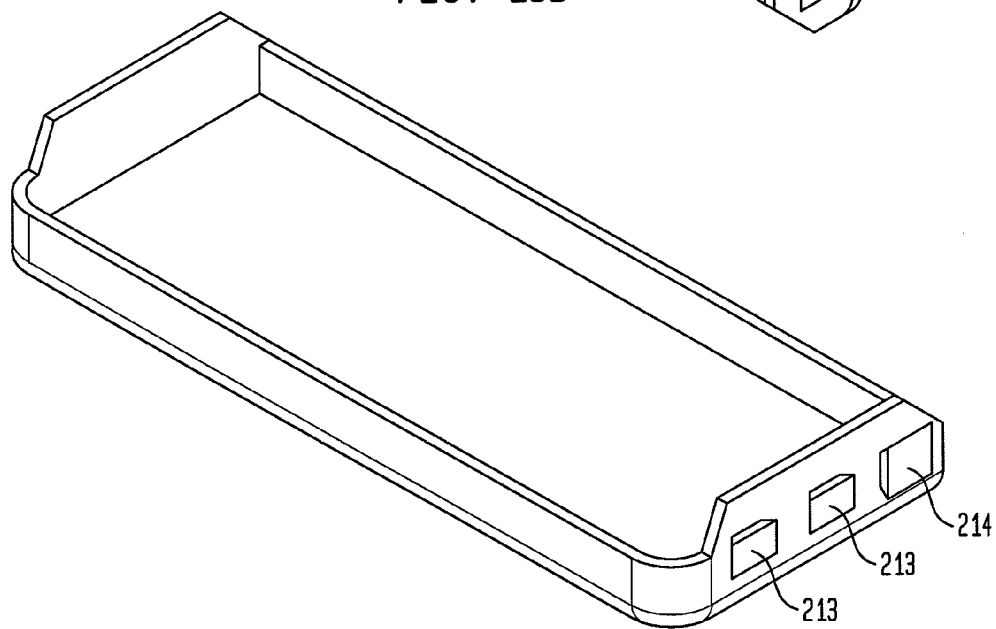

FIG. 19A shows another embodiment of a tray insert, flat tray 212. Flat tray 212 includes, vertical pins 213, horizontal pin 214, and removable insert 216. Removable insert 216 further includes slits 215. Vertical and horizontal pins are slidably and/or removably insertable into tails 20 of module 10. Vertical pins 213 are adapted to allow the flat tray 212 to be inserted vertically into module 10. Horizontal pins 214 are adapted to allow the flat tray 212 to be inserted horizontally into module 10. In an embodiment, each side of flat tray 212 includes one pin 214 adapted to insert the tray horizontally, and two pins 213 adapted to insert the tray vertically. In this embodiment, flat tray 212 may inserted in a horizontal position and/or without removable insert 216, as shown in FIG. 19B or a vertical position and/or with removable insert 216 as shown in FIG. 19A.

Figure 20:
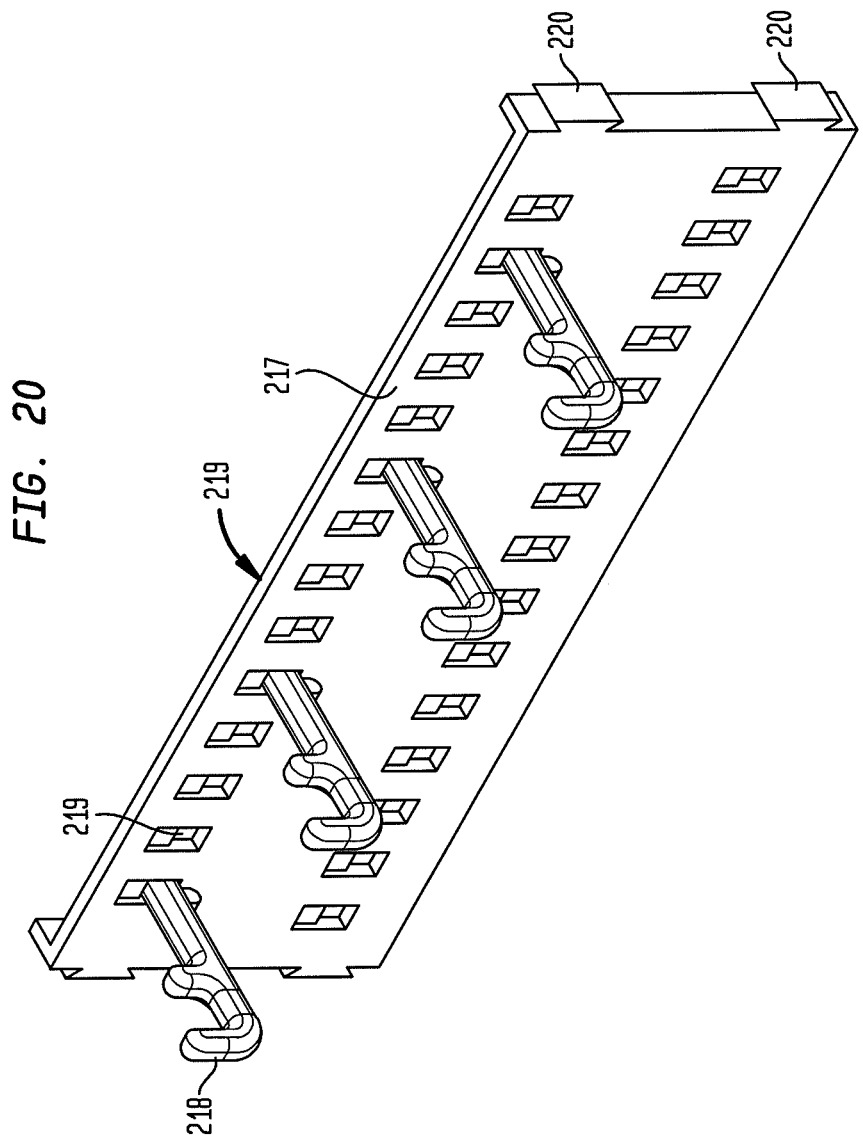
FIG. 20 is a diagram of a hook insert.

Referring now to FIG. 20, a hook insert 216 is shown. Hook insert 216 includes back panel 217 and hook 218. Back panel 217 includes a plurality of holes 219 and hook insert end pins 220. Hook 218 is fixedly insertable into one of the plurality of holes 219 of back panel 217 as shown in FIG. 20. Hook insert end pins 220 are slidably and/or removably insertable into tails 20 of module 10.

Figure 21:
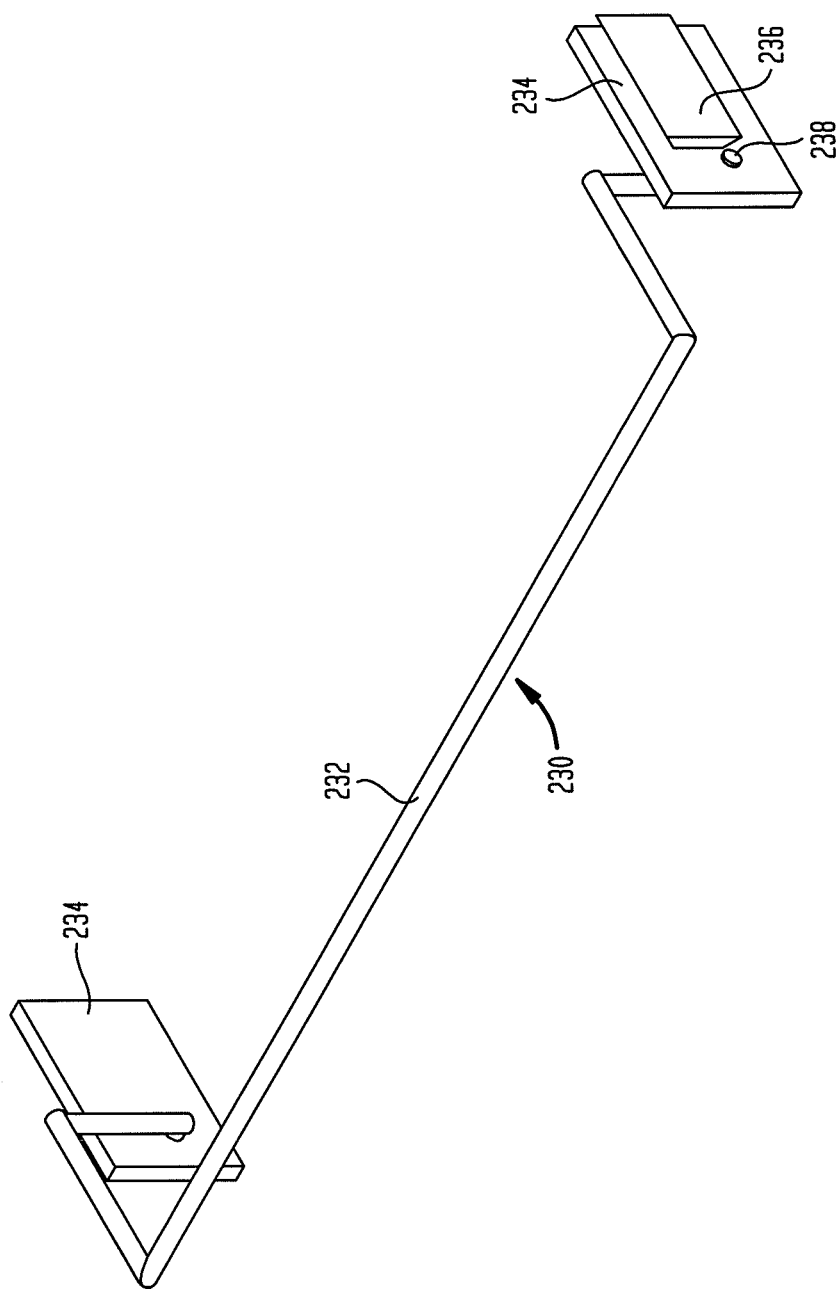
FIG. 21 is a diagram of a horizontal bar.

Referring now to FIG. 21, a horizontal bar insert 230 is shown. Horizontal bar insert 230 includes a horizontal bar 232 and two end pieces 234. Each end piece 234 includes at least one pin 236. Pin 236 is slidably and/or removably insertable into tails 20 of module 10. The horizontal bar 232 includes a peg 238 at each end which is insertable into each end piece 234. The horizontal bar is capable of pivoting or rotating around the connection of pegs 238 and end pieces 234.

Figure 22:
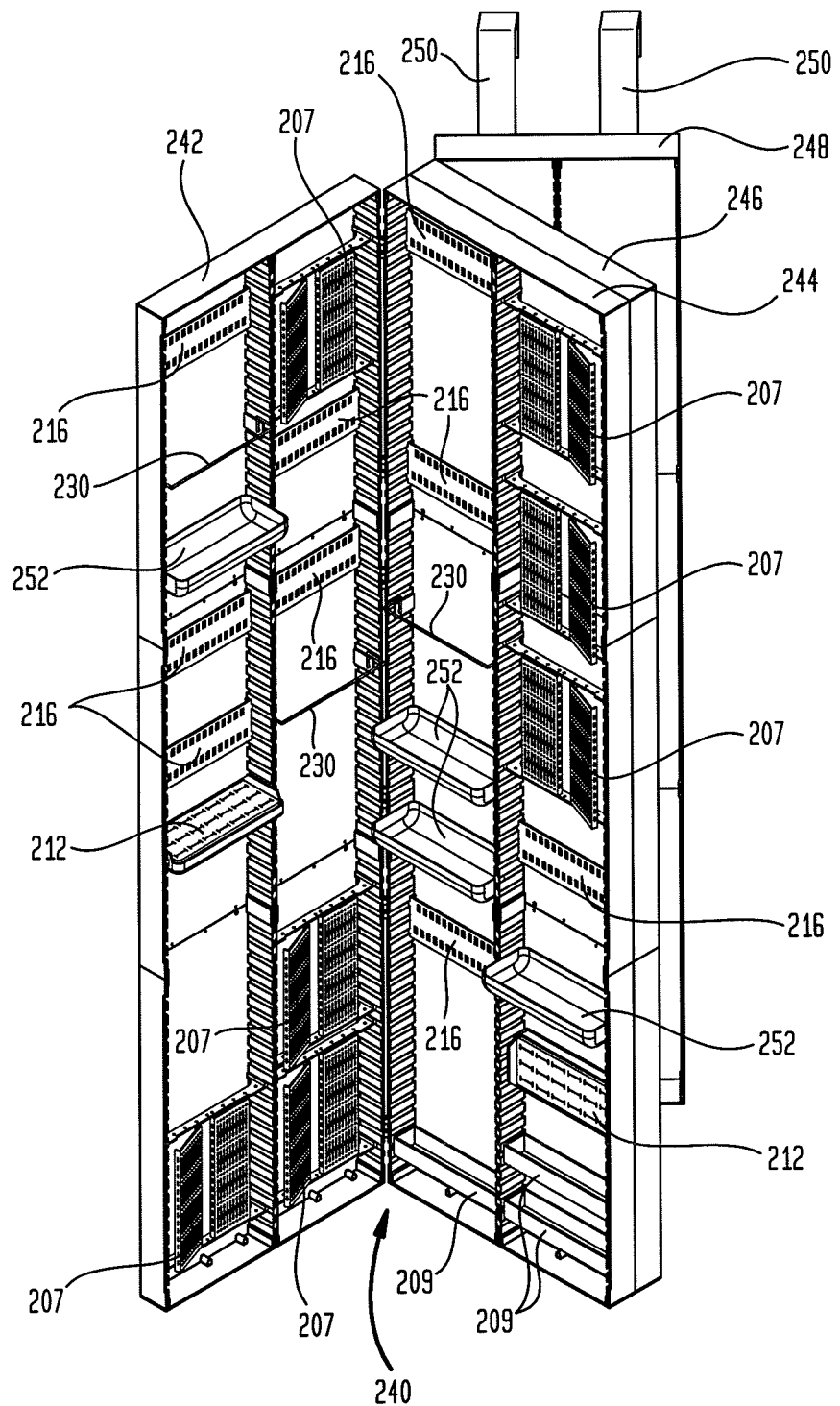
FIG. 22 is an exemplary configuration of a modular storage system.

Referring now to FIG. 22, an exemplary modular storage system assembly 240 is shown. In the exemplary embodiment of FIG. 22, modular storage system assembly 240 includes four connected modular assemblies, 242, 244, 246, 248. Each modular assembly includes six modules, similar to module 10 of FIG. 1, connected with vertical connectors 40 and U-connectors 35. Each modular assembly is connected to at least one other modular assembly to form the modular storage system assembly 240. For example, modular storage assembly 242 is connected with modular storage assembly 244 with hinge connectors 37. As shown in FIG. 22, modular assembly 242 is pivotally attached to modular assembly 244. In this exemplary embodiment modular assembly 242 acts as a door that can close the modular storage system assembly 240. Modular assembly 244 is also attached to modular assembly 246 via any fixed connection means to adjoin the respective back panels of modular assemblies 244, 246. Such connection means can be screw connections using bosses 28, blind holes 30, and holes 32 (see FIG. 4, 12-14). In this exemplary embodiment, modular assemblies 244, 246 form a two sided modular assembly that allows for inserts and storage on both sides of a flush back panel connection. Further, modular assembly 246 is connected to modular assembly 248 using hinge connectors similar to those used to connect modular assemblies 242 and 244. In the exemplary embodiment shown in FIG. 22, door hangers 250 are configured to fit over a door.

As can be seen in FIG. 22, the entire modular storage system assembly 240 can be arranged in a variety of different configurations depending on the desires of the consumer. Inserts that can be used with modular storage system assembly 240 include, but are not limited to, flag insert 207, tray insert 209, rounded tray insert 252, flat tray insert 212, hook insert 216, and horizontal bar 230. As can be seen in FIG. 22, the flat tray insert 212 can be inserted vertically (as shown in FIG. 22) or can be inserted horizontally. Additionally, rounded tray 252 includes rounded front corners to allow the opposing hinged modular assembly 242 to close without interference. Although not shown in FIG. 22, modular assemblies 246 and 248 also allow for inserts and storage.

One skilled in the art will recognize from FIG. 22 that the configuration shown is merely exemplary. Any number of modular assemblies can be attached and expanded using any connector means. For example, modular storage system assembly 240 may be configured in an "accordion" like configuration. In a further exemplary embodiment, modular storage system assembly 240 may be affixed to a wall through some connection means, e.g. screws. For example, either modular assembly 242 or modular assembly 248 may be fixedly attached to a wall through the use of screws or bolts. One of skill in the art will recognize that the inventive arrangements described herein can accommodate a nearly unlimited number of combinations and configurations. The embodiments of the present invention are not limited in this regard.

Figure 23:
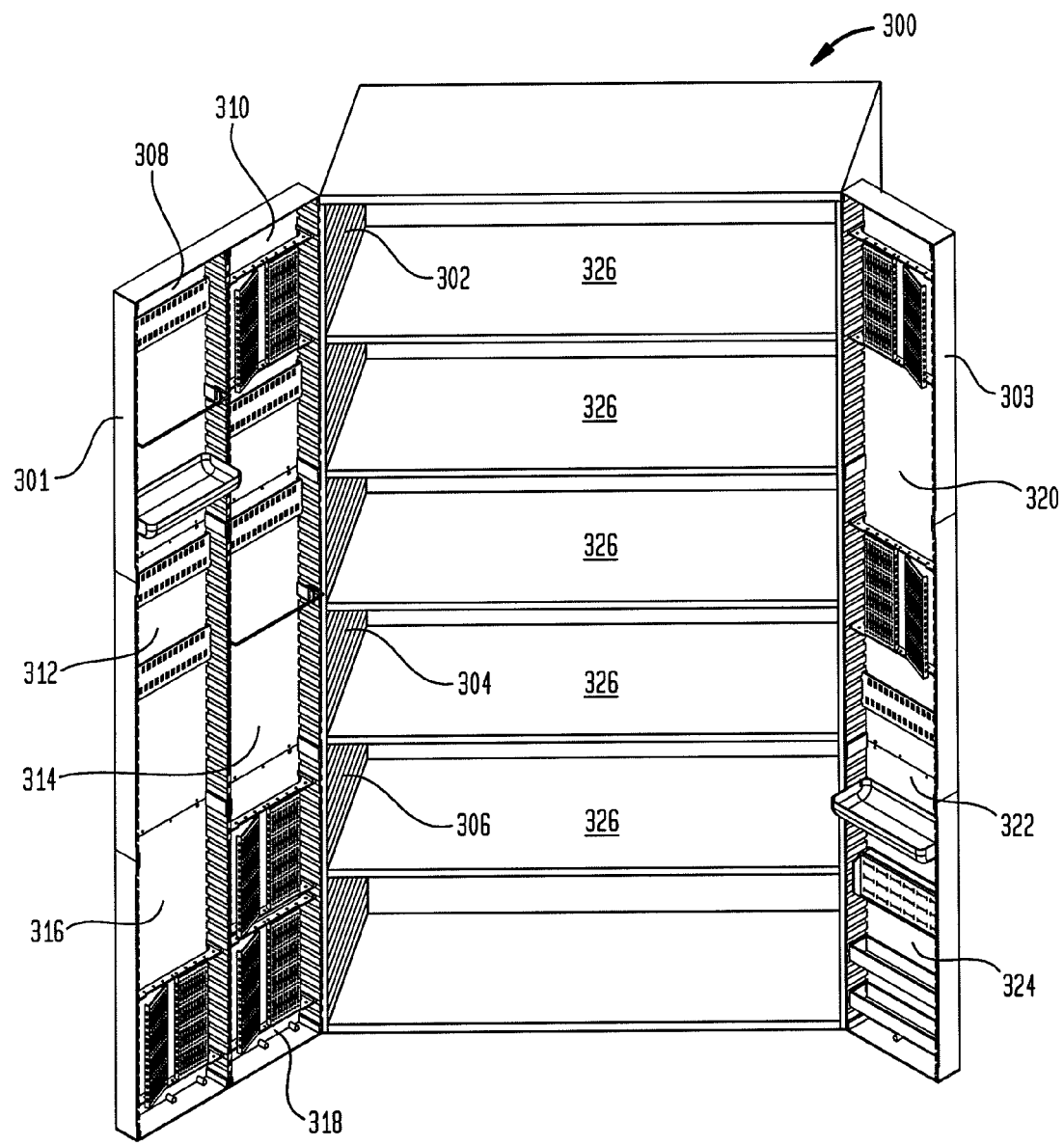
FIG. 23 is an exemplary configuration of a modular storage system.

Referring now to FIG. 23, another exemplary modular storage system assembly 300 is shown. Modular storage system assembly 300 includes three deep and wide modules 302, 304, 306. These modules have similar construction as described above in reference to FIGS. 1-4. A stated above, modules can vary in height, width, and depth. In the exemplary embodiment shown in FIG. 23, the assembly 300 also includes a plurality of shelves 326. The shelves include pins that are slidably and/or removably insertable into a series of tails cut into the side panels of modules 302, 304, 306. One of skill in the art will recognize that a variety of inserts may be included in modules 302, 304, 306, including but not limited to those described above in reference to FIGS. 15-20.

As shown in FIG. 23, modular storage system assembly 300 also includes two "door" sub-assemblies 301 and 303. As noted above, modules may be attached to expand the assembly in a horizontal and vertical directions. In the exemplary embodiment shown in FIG. 23, door sub-assembly 301 includes six smaller modules 308, 310, 312, 314, 316, 318 arranged in a two horizontal by three vertical configuration. Also shown in FIG. 23, door sub-assembly 303 includes three smaller modules 320, 322, 324 arranged in a one horizontal by three vertical configuration. One of skill in the art will recognize that the deep and wide modules 302, 304, 306 and the smaller modules 308, 310, 312, 314, 316, 318, 320, 322, 324 may be arranged in a variety of configurations without departing from the inventive concepts described herein. Further, inventive assemblies my include more or fewer modules than is shown in FIG. 23 or any other drawing. The embodiments of the present invention are not limited in this regard.

Although the invention has been illustrated and described with respect to one or more implementations, equivalent alterations and modifications will occur to others skilled in the art upon the reading and understanding of this specification and the annexed drawings. In addition, while a particular feature of the invention may have been disclosed with respect to only one of several implementations, such feature may be combined with one or more other features of the other implementations as may be desired and advantageous for any given or particular application. Thus, the breadth and scope of the present invention should not be limited by any of the above described embodiments. Rather, the scope of the invention should be defined in accordance with the following claims and their equivalents.

The invention claimed is:

1. A modular storage assembly (240, 300), comprising:
   a first module (10) comprising:
      a first rectangular, substantially flat back panel (12);
      a first left and a right side panel (14a, 14b), said first left and right side panels (14a, 14b) perpendicularly attached to opposite sides of said rectangular back panel (12), and having a substantially flat outer side and a ridged inner side comprised of alternating evenly spaced pins (18) and tails (20), wherein each end of said first left and right side panels (14a, 14b) terminates with an end pin (26), wherein said first right and left side panels (14a, 14b) include a plurality of notches (22) along a side of said first right and left side panels (14a, 14b) parallel and opposite to said rectangular back panel (12), wherein each of said plurality of notches (22) coincides with a tail (20); and,
      a top and a bottom panel (16) perpendicularly attached to opposite sides of said first rectangular back panel (12) perpendicular to said first left and right side panels (14a, 14b), said top and bottom panels (16) having substantially flat outer and inner sides, said inner side includes an extending member (25) at each end that is slidably insertable into a first tail (23) from each end of said right and left side panels (14a, 14b) forming a dovetail joint, wherein said end pin (26) on each side panel (14a, 14b) forms a flush corner with said top or said bottom panel (16), wherein said first module (10) forms a rectangular open box when fully assembled; and,
   a second module (10) comprising:
      a second rectangular, substantially flat back panel (12); and
      a second left and a right side panel (14a, 14b), said second left and right side panels (14a, 14b) perpendicularly attached to opposite sides of said rectangular back panel (12), and having a substantially flat outer side and a ridged inner side comprised of alternating evenly spaced pins (18) and tails (20), wherein each end of said second left and right side panels (14a, 14b) terminates with an end pin (26),
   wherein at least one of said first left and right side panels (14a, 14b) are attached to at least one of said second left and right side panels (14a, 14b) by at least one slidably insertable fastener (35, 37, 40) inserted into at least one tail (20) of each respective side panel (14a, 14b).

2. The modular storage assembly (240, 300) of claim 1, wherein said first right side panel (14b) and said second left side panel (14a) are horizontally fixedly attached, wherein said at least one slidably insertable fastener is a U shaped dovetail connector (35) that is inserted into at least one of said tails (20).

3. The modular storage assembly (240, 300) of claim 2, further comprising:
   a third module (10) that comprises:
      a third rectangular, substantially flat back panel (12); and,
      a third left and a right side panel (14a, 14b), said second left and right side panels (14a, 14b) perpendicularly attached to opposite sides of said rectangular back panel (12), and having a substantially flat outer side and a ridged inner side comprised of alternating evenly spaced pins (18) and tails (20), wherein each end of said second left and right side panels (14a, 14b) terminates with an end pin (26),
   wherein said third module (10) is adjoined to said first or second module (10) such that one of said first and second back panels (12) are in fixed contact with said third back panel (12).

4. The modular storage assembly (240, 300) of claim 1, wherein at least one of said first right and left side panels (14a, 14b) and at least one of said second right and left side panels (14a, 14b) are horizontally pivotally attached, wherein said at least one slidably insertable fastener is a hinge dovetail connector (37) that is inserted into at least one of said tails (20).

5. The modular storage assembly (240, 300) of claim 1, wherein said first side panels (14a, 14b) and said second side panels (14a, 14b) are vertically fixedly attached, wherein said at least one slidably insertable fastener is a dual pin vertical connector (40) that is inserted into said first tail (23) of each end of said first and second side panels (14a, 14b).

6. A modular storage assembly (240, 300), comprising:

a first module (10) comprising:
- a rectangular, substantially flat back panel (12); and,
- a first left and a right side panel (14a, 14b), said first left and right side panels (14a, 14b) perpendicularly attached to opposite sides of said rectangular back panel (12), and having a substantially flat outer side and a ridged inner side comprised of alternating evenly spaced pins (18) and tails (20), wherein each end of said first left and right side panels (14a, 14b) terminates with an end pin (26); and, a second module (10) that comprises:
- a second rectangular, substantially flat back panel (12); and,
- a second left and a right side panel (14a, 14b), said second left and right side panels (14a, 14b) perpendicularly attached to opposite sides of said rectangular back panel (12), and having a substantially flat outer side and a ridged inner side comprised of alternating evenly spaced pins (18) and tails (20), wherein each end of said second left and right side panels (14a, 14b) terminates with an end pin (26); and,
- a top and a bottom panel (106a, 106b, 106c) perpendicularly attached to opposite sides of said rectangular back panel (12) perpendicular to said first and second left and right side panels (14a, 14b), said top and bottom panels (106a, 106b, 106c) having a substantially flat outer side and include an extending member (25) at each end that is slidably insertable into a first tail (23) from each end of said right and left side panels (14a, 14b) forming a dovetail joint, wherein said end pin on each side panel (14a, 14b) forms a flush corner with said top or said bottom panel (106a, 106b, 106c), wherein said top and bottom panels (106b, 106c) include two additional extending members (25) allowing said first and second modules (10) to be fixedly attached side-by-side.

7. The modular storage assembly (240, 300) of claim 6, further comprising:

a third module (10) that comprises:
- a third rectangular, substantially flat back panel (12); and,
- a third left and a right side panel, said third left and right side panels perpendicularly attached to opposite sides of said rectangular back panel (12), and having a substantially flat outer side and a ridged inner side comprised of alternating evenly spaced pins (18) and tails (20), wherein each end of said third left and right side panels (14a, 14b) terminates with an end pin (26), wherein said top and bottom panels (106c) include two additional extending members (25) allowing the first, second and third modules (10) to be fixedly attached side-by-side.

8. The modular storage assembly (240, 300) of claim 6, further comprising:

a third module (10) that comprises:
- a third rectangular, substantially flat back panel (12); and,
- a third left and a right side panel (14a, 14b), said third left and right side panels (14a, 14b) perpendicularly attached to opposite sides of said rectangular back panel (12), and having a substantially flat outer side and a ridged inner side comprised of alternating evenly spaced pins and tails, wherein each end of said third left and right side panels (14a, 14b) terminates with an end pin, wherein said third module (10) is pivotally attached to at least one of said first and second modules.

9. A modular storage assembly (240, 300), comprising:

at least three modules (10) comprising:
- a rectangular, substantially flat back panel (12);
- a left and a right side panel (14a, 14b), said left and right side panels (14a, 14b) perpendicularly attached to opposite sides of said rectangular back panel (12), and having a substantially flat outer side and a ridged inner side comprised of alternating evenly spaced pins and tails, wherein each end of said left and right side panels (14a, 14b) terminates with an end pin; and
- a top and a bottom panel (16) perpendicularly removably attached to opposite sides of said rectangular back panel (12) perpendicular to said left and right side panels (14a, 14b), said top and bottom panels (16) have substantially flat outer and inner sides, said inner side includes an extending member (25) at each end that is slidably insertable into a first tail (23) from each end of said right and left side panels (14a, 14b) forming a dovetail joint, wherein said end pin (26) on each side panel (14a, 14b) forms a flush corner with said top or said bottom panel (16; and at least one insert (201, 209, 212, 219, 230, 252), wherein said at least one insert includes two ends and each end includes at least one pin (206, 210, 213, 214, 220, 236) which is slidably insertable into said tails (20) of said left and right side panels (14a, 14b), wherein said at least three modules (10) are connected with at least one slidably insertable connector (35, 37, 40) that is slidably insertable into at least one tail (20) of said left and right side panels (14a, 14b), wherein at least two of said at least three modules (10) are fixedly connected, wherein said back panels (12) of said at least two modules (10) are substantially in contact with each other;

wherein at least two of said at least three modules (10) are pivotally connected with a slidably insertable connecter that is a hinge connecter (37), and, wherein at least two of said at least three modules (10) are fixedly connected with a slidably insertable connector that is one of a U-connector (35) and a dual pin vertical connector (40).

* * * * *